US006379907B1

(12) United States Patent
Liao et al.

(10) Patent No.: US 6,379,907 B1
(45) Date of Patent: Apr. 30, 2002

(54) DIAGNOSTIC METHOD USING EXPRESSION OF MN/CA9 PROTEIN IN AGUS PAP SMEARS

(75) Inventors: Shu-Yuan Liao, Anaheim; Eric J. Stanbridge, Corona del Mar, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/461,938

(22) Filed: Dec. 15, 1999

Related U.S. Application Data

(60) Provisional application No. 60/147,556, filed on Aug. 5, 1999.

(51) Int. Cl.[7] ...................... G01N 33/574; G01N 33/53; G01N 33/567; C12Q 1/00; C12Q 1/68
(52) U.S. Cl. .............. 435/7.23; 435/4; 435/6; 435/7.1; 435/7.2; 436/64; 436/501; 436/503
(58) Field of Search ........................... 530/387.1; 435/4, 435/6, 7.1, 7.2, 7.23; 436/64, 501, 503

(56) References Cited

U.S. PATENT DOCUMENTS

| | | |
|---|---|---|
| 5,346,831 A | 9/1994 | Carrico et al. |
| 5,387,676 A | 2/1995 | Zavada et al. |
| 5,955,075 A | 9/1999 | Zavada et al. |
| 5,972,353 A | 10/1999 | Zavada et al. |
| 5,981,711 A | 11/1999 | Zavada et al. |

(List continued on next page.)

OTHER PUBLICATIONS

Stanbridge, Eric, *A protein antigen holds promise for better cervical cancer detection, UC Irvine researcher reports*, UCI News, Mar. 23, 1998.
Lett, David N., *Transatlantic antigen enhances reliability of cervical cancer pap test: clinical trials pending*, BioWorld Today Archives, Mar. 24, 1998.

*Cervical marker can help resolve ambiguous pap smears*, Diagnostic Intelligence, vol. 10, No. 5, May 1998, p. 2, col. 1.
*New Tests Unveiled that Detect Cancer*, San Francisco Chronicle, Mar. 27, 1998, p. A8.
*New Test Could End Pap Smear 'Gray Area'*, Los Angeles Times, Mar. 24, 1998, p. B4.
NIH Consensus Statement (1) Cervical Cancer. 1996; 14:1–18.
McGonigle KF, and Berek JS. Early stage squamous cell and adenocarcinoma of the cervix. Curr. Opin. Obstet. Gynecol., 1992; 4:109–119.
Koss LG. Cervical (Pap) smear. New directions. Cancer (Phila.), 71 (suppl.); 1993; p. 1406 only.
Ayer B, Pacey F, Greenberg M, Bousfield L. The cytologic diagnosis of adenocarcinoma in situ of the cervix uteri and related lesions. I. Adenocarcinoma in situ. Acta Cytol., 1987;31:397–411.
Pacey NF. Glandular neoplasms of the uterine cervix. In: Bibbo M., ed. Comprehensive Cytopatholog. Philadelphia: WB Saunders, 1991;243–255.
National Cancer Institute Workshop. The revised Bethesda System for reporting cervical/vaginal cytologic diagnosis: report of the 1991 Bethesda Workshop, JAMA, 1992;267:1892.

(List continued on next page.)

*Primary Examiner*—Sheela Huff
*Assistant Examiner*—Jennifer Hunt
(74) *Attorney, Agent, or Firm*—Fulbright & Jaworski L.L.P.

(57) ABSTRACT

Determining the presence of cancerous or pre-cancerous cervical lesions from AGUS-diagnosed Pap smear cells by observing the distribution of MN/CA9 antigen expressed on atypical or normal cells and diagnosing (a) significant lesions when MN/CA9 antigen is observed on atypical cells, (b) low grade lesions when MN/CA9 antigen is absent from atypical cells but is present on normal endocervical cells, and (c) a benign condition when MN/CA9 antigen is absent from both atypical cells and normal endocervical cells.

9 Claims, 7 Drawing Sheets

U.S. PATENT DOCUMENTS

| | | | |
|---|---|---|---|
| 5,989,838 A | 11/1999 | Zavada et al. |
| 6,004,535 A | 12/1999 | Zavada et al. |
| 6,027,887 A | 2/2000 | Zavada et al. |
| 6,051,226 A | 4/2000 | Zavada et al. |
| 6,069,242 A | 5/2000 | Zavada et al. |
| 6,093,548 A | 7/2000 | Zavada et al. |
| 6,204,370 B1 | 3/2001 | Zavada et al. |
| 6,297,041 B1 | 10/2001 | Zavada et al. |
| 6,297,051 B1 | 10/2001 | Zavada et al. |

OTHER PUBLICATIONS

Kurman RJ, Solomon D. In The Bethesda system for Reporting Cervical/Vaginal Cytologic Diagnoses. New York: Springer–Verlag, 1994;64–76.

Lee KR. Atypical glandular cells in cervical smears from women who have undergone cone biopsy. A potential diagnostic pitfall. Acta. Cytol., 1993;37:705–709.

Pacey F, Ayer B, Greenberg M. The cytologic diagnosis of adenocarcinoma in situ of the cervix uteri and related lesions. III. Pitfalls in diagnosis. Acta. Cytol., 1988;32:325–330.

Yahr LJ, Lee KR. Cytologic findings in microglandular hyperplasia of the cervix. Diagn. Cytopathol. 1991;7:248–251.

Novotny DB, Maygarden SJ, Johnson DE, Frable WJ. Tubal metaplasia. A frequent potential pitfall in the cytologic diagnosis of endocervical glandular displasia on cervical smears. Acta. Cytol., 1992;36:1–10.

Koss LG. Diagnostic cytology and its histopathologic bases. vol. 1 4th ed. Philadelphia; JB Lippincott: 1992:387:452–454.

Wilbur DC, Mulford DM, Sickel JZ, Atkinson KM. The problem of endocervical atypia: new cytologic presentations of normal endocervical cells. Mod. Pathol., 1994;38:808.

Goff BA., Atanasoff P, Brown E, Muntz HG, Bell DA, Rice LW. Endocervical glandular atypia in Pananicolaou smears. Obstet. Gynecol., 1992;79:101–104.

Lee KR, Manna EA, John T.st. Atypical endocervical glandular cells: accuracy of cytologic diagnosis. Diagn. Cytopathol. 1995;13:202–208.

Nasu I, Meurer W, Fu YS. Endocervical glandular atypia and adenocarcinoma: A correlation of cytology and histology., Int. J. Gynecol. Pathol., 1993;12:208–218.

Taylor R, Guerriere J, Nash JD, Henry MR, O'Conner DM. Atypical cervical ctyology: Colposcopic follow–up using The Bethesda System, J. Reprod. Med., 1993;38:443–447.

Kennedy AW, Salmieri S, Wirth SL, Biscotti CV, Tuason LJ, Travarca MJ. Results of the clinical evaluation of atypical glandular cells of undetermined significance (AGCUS) detected on cervical cytology screening. Gynecol. Oncol., 1996;63:141–18.

Bose S, Kanna V, Kline TS. Abnormal endocervical cells. Really abnormal? Really endocervical? Am.J. Clin. Pathol., 1994;101:708–713.

Zavada J, Zavadova Z, Pastorekova S, Ciampor F, Postorek J, Zelnik V. Expression of MaTuMN protein in human tumor cultures and in clinical specimens. Int. J. Cancer 1993;54:268–274.

Pastorek J, Pastorekova S, Callebaut I, Mornon JP, Zelnik V, Opavsky R, Zatovicova M, Liao S, Portelle D, Stanbridge EJ, Zavada J, Burny A, Kettmann R. Cloning and characterization of MN, a human tumor–associated protein with a domain homologous to carbonic anhydrase and a putative helix–loop–helix DNA binding segment. Oncogene 1994;9:2877–2888.

Liao SY, Brewer C, Zavada J, Postorek J, Pastorekova S, Manetta A, Berman ML, DiSaia PJ, Stanbridge EJ. Identification of the MN antigen as a diagnostic biomarker of cervical intraepithelial squamous and glandular neoplasia and cervical carcinomas. Am.J.Pathol., 1994; 145:598–609.

Liao SY, Stanbridge EJ. Expression of the MN antigen in cervical Papanicolaou smears is an early diagnostic biomarker of cervical dysplasia. Canc. Epid. Biom. Prev., 1996;5:549–557.

Hsu SM, Raine L, Fanger H. Use of avidin–biotin peroxidase complex (ABC) in immunoperoxidase techniques: a comparison between ABC and unlabeled antibody (PAP) procedures. J. Histochem. Cytochem., 1981;29:577–580.

Crum CP, Cibas ES, Lee KR. Criteria for grading squamous intraepithelial lesions. In: Pathology of Early Cervical Neoplasia, New York: Churchill Livingstone, 1997;47–91.

Kurman RJ, Norris HJ, Wilkinson E. Tumors of the cervix, vagina, and vulva: In: Atlas of Tumor Pathology, 3rd series, fasc. 4, Armed Forces Institute of Pathology, 1992;37–139.

Miller BE, Flax SD, Arheart K, Photopulos G. The presentation of adenocarcinoma of the uterine cervix. Cancer 1993;72:1281–1285.

Crum CP, Cibas ES, Lee KR. Glandular precursors, adenocarcinomas, and their mimics. In: Pathology of early cervical neoplasia, New York: Churchill Livingstone, 1997;177–240.

Kim HS, Underwood D, Frable WJ. Adenocarcinoma in the cervicovaginal Papanicolaou smear: analysis of a 12–year experience. Diagn. Cytopathol., 1991;7:119–124.

Raab SS, Geisinger KR, Silverman JF, Thomas PA, Stanley MW. Interobserver variability of a Papanicolaou smear diagnosis of atypical glandular cells of undetermined significance. Am.J.Clin.Patjol., 1998;110:653–659.

Raab SS. Isaacson C, Layfield LJ, Lenel, JC, Slagel, DD, Thomas PA. Atypical glandular cells of undetermined significance: cytologic criteria to separate clinically significant from benign lesions. Am.J.Clin.Pathol., 1995;104:574–582.

Raab AA, Snider TE, Potts SA, McDaniel HL, Robinson RA, Nelson DL, Sigman JD, Thomas PA. Atypical glandular cells of undetermined significance. Diagnostic accuracy and interobserver variability using select cytologic criteria. Am.J.Clin.Pathol., 1997;107:299–307.

DiTomasso JP, Ramzy I, Mody DR. Glandular lesions of the cervix: Validity of cytologic criteria used to differentiate reactive changes, glandular intraepithelial lesions and adenocarcinoma. Acta. Cytol., 1996;40:1127–1135.

Casper, GR, Ostor AG, Quinn MA. A Clinicopathologic Study of Glandular Dysplasia of the Cervix. Gynecologic Oncology., 1997;64:166–170.

DIAGNOSTIC METHOD USING EXPRESSION OF MN/CA9 PROTEIN IN AGUS PAP SMEARS

CROSS REFERENCE TO RELATED APPLICATIONS

This application claims the benefit of Provisional Patent Application No. 60/147,556, filed Aug. 5, 1999.

BACKGROUND OF THE INVENTION

Carcinoma of the cervix is one of the most common malignancies in women, and worldwide it is second only to breast cancer in both incidence and mortality (NIH Consensus Statement (1) Cervical Cancer. 1996.14:1–18). In developed countries in general, and the United States in particular, the wide acceptance of the Pap smear screening program has resulted in dramatic decreases in the incidence of, and mortality from, cervical cancer. However, a recent survey conducted in United States still showed that an estimated 15,700 women were diagnosed with invasive cervical carcinoma, and an estimated 4,900 women died of cervical cancer per annum (NIH Consensus Statement (1) Cervical Cancer. 1996.14:1–18). Moreover, the incidence of adenocarcinorna has tripled in the past two decades (McGonigle K F, and Berek J S. Early stage squamous cell and adenocarcinoma of the cervix. Curr. Opin. Obstet. Gynecol., 1992. 4:109–119), and currently represents up to 25% of all cervical cancers diagnosed (Miller B E, Flax S D, Arheart K, Photopulos G. The presentation of adenocarcinoma of the uterine cervix. Cancer 1993. 72:1281–1285; and Crum C P, Cibas E S, Lee K R. Glandular precursors, adenocarcinomas, and their mimics. In: Pathology of early cervical neoplasia. New York: Churchill Living stone, 1997. 177–240).

Many factors have been implicated in the relatively high incidence of cervical cancer but the inherently high rate of false negatives appears to be one of the major concerns in the current system of screening. The errors have been attributed, in part, to technical problems, but also may well be based primarily on human factors that are not remedied readily by rules and regulations (Kos L G. Cervical (Pap) smear. New directions. Cancer (Phial.), 71 (suppl.); 1993. 1406–1412).

In recent years, the use of new cervical sampling devices (e.g. cytobrushes) have improved the detection of both glandular and squamous neoplasms involving the endocervical canal. However, the increased endocervical cell yields have also created many new patterns of benign and neoplastic endocervical cytology with significant overlapping features. These patterns are unfamiliar to cytologists in routine daily practice. This uncertainty has been reflected in an increase in the cytologic diagnosis of endocervical glandular atypia.

The morphological criteria for a Pap smear diagnosis of AIS and adenocarcinoma have been well described (Ayer B, Pacey F, Greenberg M, Bousfield L. The cytologic diagnosis of adenocarcinoma in situ of the cervix uteri and related lesions. I. Adenocarcinoma in situ. Acta Cytol., 1987. 31:397–411; and Pacey N F. Glandular neoplasms of the uterine cervix. In: Bibbo M, ed. Comprehensive Cytopatholog. Philadelphia: W B Saunders, 1991. 243–255). However, false-negative rates of up to 40 percent in Pap smears from women later found to have AIS and/or invasive endocervical adenocarcinoma have been reported (Crum et al.,1997, 177–240; and Kim H S, Underwood D, Frable W J. Adenocarcinoma in the cervicovaginal Papanicolaou smear: analysis of a 12-year experience. Diagn. Cytopathol., 1991. 7:119–124). The earlier misdiagnosing of AIS/CA was attributed to the presence of low numbers of endocervical glandular cells in the Pap smears, and/or technical artifacts. However, studies have also indicated that human error may play an important role. This includes the incorrect diagnosis of dysplastic glandular cells as exfoliative endometrial cells and/or reactive endocervical cells (Kos et al., 1993; and Lee K R, Manna E A, St. John T. Atypical endocervical glandular cells: accuracy of cytologic diagnosis. Diagn. Cytopathol. 1995. 13:202–208).

In an attempt to clarify the situation, the Bethesda System committee in 1988 established cytologic criteria for atypical glandular cells, and proposed a new diagnostic terminology with a subclassification scheme, in order to aid in patient triage. It was recommended that endocervical glandular abnormalities that exceed reactive change but fall short of invasive adenocarcinoma be reported as atypical glandular cells of undetermined significance (AGUS) (National Cancer Institute Workshop. The revised Bethesda System for reporting cervical/vaginal cytologic diagnosis: report of the 1991 Bethesda Workshop. JAMA, 1992. 267:1892; and Kurman R J, Solomon D. In The Bethesda System for Reporting CervicalNaginal Cytologic Diagnoses. New York: Springer-Verlag, 1994. 64–76). Up to 1.25 million American women receive a diagnosis of AGUS annually (Raab S S, Geisinger K R, Silverman J F, Thomas P A, Stanley M W. Interobserver variability of a Papanicolaou smear diagnosis of atypical glandular cells of undetermined significance. Am. J. Clin. Pathol., 1998. 110:653–659). However, the results of this subclassification have yet to be proven clinically effective.

A broad morphologic spectrum of benign and neoplastic lesions are included in the category of AGUS. These include atypical endocervical repair, endometriosis, microglandular hyperplasia, tubal metaplasia, squamous intraepithelial lesion (SIL) with glandular involvement, and glandular dysplasia, and adenocarcinoma (Lee K R. Atypical glandular cells in cervical smears from women who have undergone cone biopsy. A potential diagnostic pitfall. Acta. Cytol., 1993. 37:705–709; Pacey F, Ayer B, Greenberg M. The cytologic diagnosis of adenocarcinoma in situ of the cervix uteri and related lesions. III. Pitfalls in diagnosis. Acta. Cytol., 1988. 32:325–330; Yahr U, Lee K R. Cytologic findings in microglandular hyperplasia of the cervix. Diagn. Cytopathol. 1991. 7:248–251; Novotny DB, Maygarden S J, Johnson D E, Frable W J. Tubal metaplasia. A frequent potential pitfall in the cytologic diagnosis of endocervical glandular dysplasia on cervical smears. Acta. Cytol., 1992. 36:1–10; Pacey et al., 1991; and Kos L G. Diagnostic cytology and its histopathologic bases. Vol. 1. 4th ed. Philadelphia; J B Lippincott: 1992. 387:452–454).

Several laboratories have conducted follow-up studies in those cases diagnosed as endocervical atypia. The results indicate that approximately 40% of AGUS cases represent high grade SIL, adenocarcinoma in-situ (AIS), or carcinoma, and correspondingly 60% represent benign or insignificant lesions. A surprising range (15–58%) of patients had significant lesions (HSIL, AIS/CA) in follow-up biopsies, after receiving a Pap smear diagnosis of AGUS. Furthermore, only a small fraction of the significant lesions were glandular neoplasms (AIS/CA). Thus, the AGUS diagnosis appears to be a misnomer inasmuch that many AGUS lesions are not glandular at all (Wilbur D C, Mulford D M, Sickel J Z, Atkinson K M. The problem of endocervical atypia: new cytologic presentations of normal endocervical cells. Mod. Pathol., 1994. 38:808; Goff B A., Atanasoff P, Brown E, Muntz H G, Bell D A, Rice L W. Endocervical glandular atypia in Papanicolaou smears. Obstet. Gynecol., 1992. 79:101–104; Lee et al., 1995; Nasu I, Meurer W, Fu Y S. Endocervical glandular atypia and adenocarcinoma: A correlation of cytology and histology., Int. J. Gynecol. Pathol., 1993. 12:208–218; Taylor R, Guerriere J, Nash J D, Henry M R, O'Conner D M. Atypical cervical cytology: Colposcopic follow-up using The Bethesda System, J. Reprod. Med., 1993. 38:443–447; Kennedy A W, Salmieri S S, Wirth S L, Biscotti C V, Tuason L J, Travarca M J. Results of the clinical evaluation of atypical glandular cells of undetermined significance (AGUS) detected on cervical cytology screening. Gynecol. Oncol., 1996. 63:14–18; and Bose S, Kannan V, Kline T S. Abnormal endocervical cells. Really abnormal! Really endocervical! Am. J. Clin. Pathol., 1994. 101:708–713).

There have been many attempts to define cytologic criteria that aid in the diagnosis of glandular lesions of the cervix, with the goal of separating neoplastic glandular cells from reactive changes and squamous neoplasia. Yet, there remains poor agreement among cytopathologists in reclassifying lesions originally diagnosed as AGUS, and in separating clinically significant from benign AGUS lesions (Raab et al., 1998; Novotny et al., 1992; Nasu et al.,1993; Raab S S, Isacson C, Layfield L J, Lenel, J C, Slagel, D D, Thomas P A. Atypical glandular cells of undetermined significance: cytologic criteria to separate clinically significant from benign lesions. Am. J. Clin. Pathol., 1995. 104:574–582; Raab S S, Snider T E, Potts S A, McDaniel H L, Robinson R A, Nelson D L, Sigman J D, Thomas P A. Atypical glandular cells of undetermined significance. Diagnostic accuracy and interobserver variability using select cytologic criteria. Am. J. Clin. Pathol., 1997. 107:299–307; and DiTomasso J P, Ramzy I, Mody D R. Glandular lesions of the cervix.: Validity of cytologic criteria used to differentiate reactive changes, glandular intraepithelial lesions and adenocarcinoma. Acta. Cytol., 1996. 40:1127–1135).

This diagnostic uncertainty has posed a particular dilemma in clinical management decisions, both from a cost-benefit standpoint and a desire not to subject patients to unnecessary invasive procedures. Therefore, there is a need for a useful discriminator of AGUS diagnoses that can separate glandular cells that are atypical due to reactive-reparative changes from cells that are atypical due to dysplasia and carcinoma.

Recently, a novel antigen, termed MN/CA9, has been described. It is a transmembrane glycoprotein that was discovered in the cervical adenocarcinoma cell line, Hela (Zavada J, Zavadova Z, Pastorekova S, Ciampor F, Pastorek J, Zelnik V. Expression of MaTu-MN protein in human tumor cultures and in clinical specimens. Int. J. Cancer 1993. 54:268–274). The gene encoding the MN/CA9 product is unusual—the only homologous functional domain identified to date being a carbonic anhydrase domain. Evidence supporting the role of the MN/CA9 protein in neoplastic progression includes its association with the tumorigenic phenotype in human cell hybrids and neoplastic transformation of mouse 3T3 cells following transfection with MN cDNA (Zavada et al., 1993; and Pastorek J, Pastorekova S, Callebaut I, Morrion J P, Zelnik V, Opavsky R, Zatovicova M, Liao S, Portelle D, Stanbridge E J, Zavada J, Burny A, Kettmann R. Cloning and characterization of M N, a human tumor-associated protein with a domain homologous to carbonic anhydrase and a putative helix-loop-helix DNA binding segment. Oncogene 1994. 9:2877–2888). A preliminary screen of clinical specimens indicated that expression of MN/CA9 protein is restricted to very few normal tissues, but significant levels of expression were noted in certain malignancies, including cervical neoplasms (Pastorek et al., 1994).

A study of several hundred benign and neoplastic cervical specimens has shown that MN/CA9 is expressed in all cases of AIS and in more than 90% of cervical squamous neoplasms. High levels of MN/CA9 protein expression were frequently observed in the normal-looking endocervical cells in regions adjacent to dysplastic tissues but the normal cervix does not express MN/CA9 protein. In addition, a study of 305 Pap smears has also indicated that the MN/CA9 expression seen in exfoliative cells in Pap smears recapitulates MN/CA9 expression in the corresponding tissue sections of the cervix. Virtually all atypical glandular cells derived from AIS and adenocarcinoma expressed high levels of MN antigen, whereas endocervical cells obtained from benign cervices were negative (Liao S Y, Brewer C, Zavada J, Pastorek J, Pastorekova S, Marietta A, Berman M L, DiSaia P J, Stanbridge E J. Identification of the MN antigen as a diagnostic biomarker of cervical intraepithelial squamous and glandular neoplasia and cervical carcinomas. Am. J. Pathol., 1994. 145: 598–609; Liao S Y, Stanbridge E J. Expression of the MN antigen in cervical Papanicolaou smears is an early diagnostic biomarker of cervical dysplasia. Canc. Epid. Biom. Prev., 1996. 5:549–557).

While these results have shown that expression of the MN/CA9 antigen can indicate AIS and adencarcinoma, they have not enabled reliable distinction between high grade and low grade lesions and benign conditions. Enabling such a distinction is critical to meaningful clinical diagnosis. The deadly harm caused by false negatives, and the anguish and expense caused by false positives demands a more reliable clinical procedure.

BRIEF SUMMARY OF THE INVENTION

The present invention fulfills the need for a more accurate diagnosis of AGUS than the current routine conventional Pap smear screening. The invention provides new insight into the distribution of MN/CA9 antigen on atypical and/or normal cells on AGUS-diagnosed Pap smear specimens and serves as a clinical roadmap enabling MN/CA9 antigen to at last serve as a powerful diagnostic biomarker for cancerous or pre-cancerous conditions.

Specifically, the present invention for the first time provides a reliable comprehensive method to determine the presence of cancerous or pre-cancerous cervical lesions from Pap smear cells that have been cytologically diagnosed as atypical glandular cells of undetermined significance (AGUS) under the Bethesda System of terminology. The AGUS-diagnosed Pap smear cells are subjected to a procedure that detects expression of MN/CA9 antigen, such as immunohistochemistry or in situ cytohybridization. AGUS-diagnosed Pap smears typically lack readily ascertainable dysplastic cells, but do include atypical and normal endocervical cells. It is the distribution of MN/CA9 antigen observed on atypical or normal cells that is used to diagnose the presence of significant or low grade lesions. More specifically, significant lesions, including adenocarcinoma, invasive carcinoma (CA), or high grade squamous intraepithelial lesions (HSIL) are diagnosed when MN/CA9 antigen is observed on atypical cells. Low grade lesions, including low grade squamous intraepithelial lesions (LSIL) or atypia, are diagnosed when MN/CA9 antigen is absent from atypical cells but is present on normal endocervical cells. A benign condition is diagnosed when MN/CA9 is absent from atypical and normal endocervical cells.

In preferred versions of the present invention, not only the presence, but the nature of, a significant lesion is diagnosed whenever MN/CA9 antigen is observed on atypical cells. In one embodiment, the presence of adenocarcinoma, including adenocarcinoma in situ (AIS) and invasive adenocarcinoma, is diagnosed when MN/CA9 antigen is detected on atypical cells in a columnar or honeycomb configuration. In another embodiment, the presence of HSIL is diagnosed when MN/CA9 antigen is detected on atypical cells in a tight cluster.

Accordingly, the methods of the present invention overcome problems of uncertainty and false negatives associated with the AGUS diagnosis for Pap smear specimens. In addition, the method discriminates among atypical Pap smears that are associated with significant lesions, low grade lesions or a benign condition.

BRIEF DESCRIPTION OF THE DRAWINGS

These and other features, aspects, and advantages of the present invention will become better understood with regard to the following description, appended claims, and accompanying drawings, where:

DETAILED DESCRIPTION OF THE INVENTION

Figure 1:
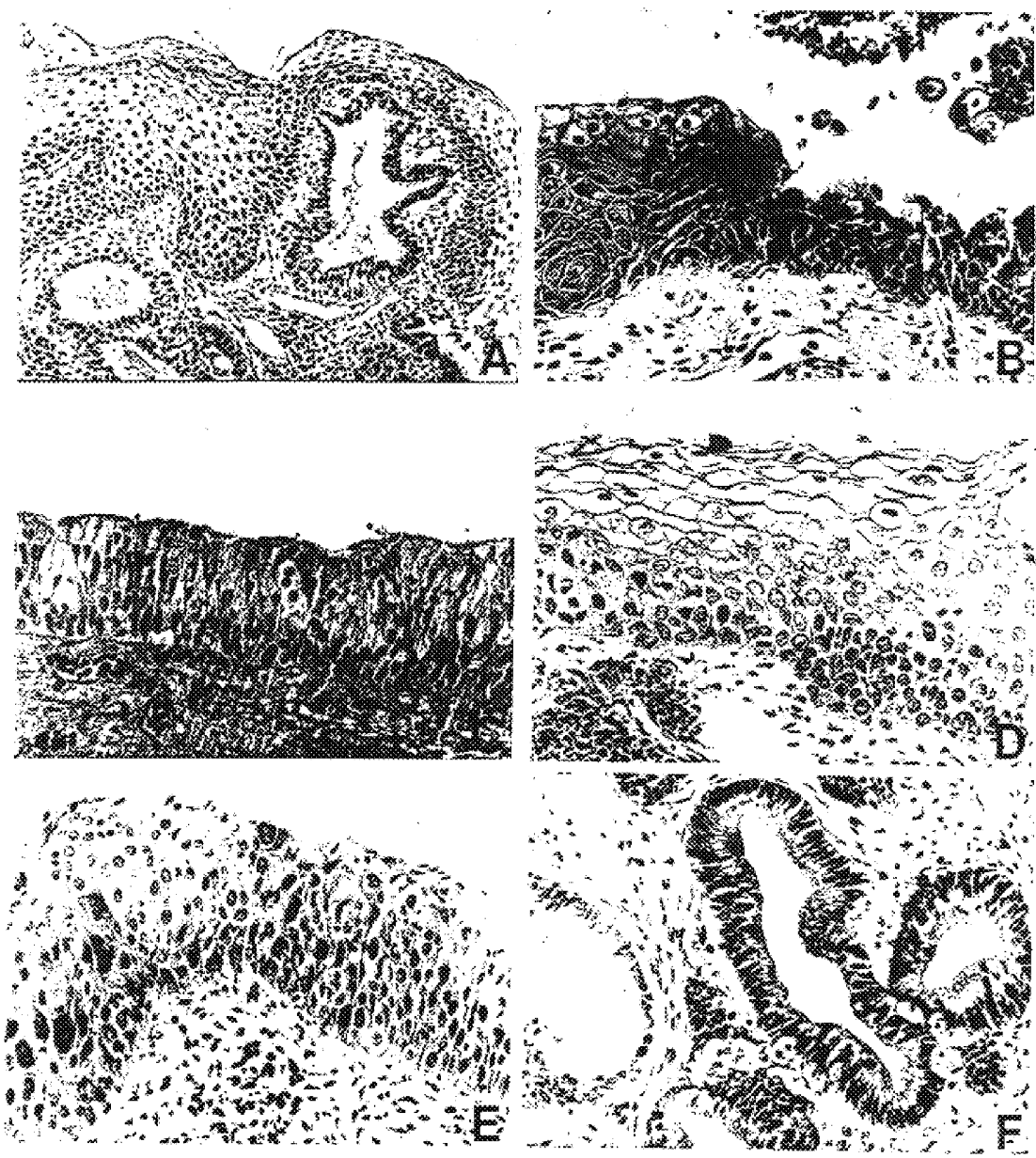
FIG. 1 shows a spectrum of squamous and glandular alterations to illustrate the criteria for diagnosis of atypia, preneoplastic and neoplastic lesions: Panel A is a normal cervix showing orderly arrangement of squamous and glandular epithelium, Panel B is an example of atypical squamous metaplasia (left) and reserve cell proliferation (right), Panel C is an example of glandular atypia with epithelial stratification, Panels D and E illustrate LSIL and HSIL, respectively, and Panel F is an example of AIS (Magnification: A 100×, B–F 200×)

The method of the present invention entails examining of the levels and distribution of expression of MN/CA9 antigen to confirm diagnoses obtained by cytological examinations, e.g., Pap smears, when observing atypical glandular cells of undetermined significance. A positive result serves as an early marker of dysplasia even in the absence of its clinical manifestations.

I. Obtain Pap Smear

The first step in any cytological diagnostic method is obtaining suitable Pap smear cells for review. In a conventional Pap smear test, a cytologist examines an exfoliative cell specimen, obtained by scraping some cells from the lining of the cervix, smearing the cells onto a slide and staining with Papanicolaou stain. The cytologist examines the stained smears for the presence of abnormal-looking cells that indicate the presence of a malignant condition. The term "malignant condition" refers to the presence of dysplasia including adenocarcinoma in situ (AIS), invasive carcinoma (CA), neoplastic, malignant or tumor cells or the like.

In the method of the invention an exfoliative cell specimen is obtained from a patient, who may or may not harbor a malignant condition. The specimen may be obtained by rotating a cervical sampling device, such as a swab, spatula, or cytobrush along a portion of cervix or vaginal mucosa to obtain a cell sample. A suitable specimen will contain endocervical cells with squamous and/or glandular cells.

The exfoliative cell specimen is generally smeared on the slide to provide a thin layer of the specimen on the surface of the slide. However, the manual observation of cellular abnormalities or the automated analysis of cytological material can be optimized by preparing "monolayers" of cells on the specimen slides. A "monolayer" is defined as substantially a two-dimensional layer of uniformly distributed cellular material, predominantly made up of single cells and small clusters of cells. Previous methods for disaggregating the exfoliated cells and using such disaggregated cells to produce a "monolayer" of cells on a specimen slide have included ultrasonic vibration, shearing with a rotor, syringing, forced filtration, centrifugation, sedimentation, and filter transfer. Examples of such techniques include the automated ThinPrep® System (Cytyc Corporation, Marlborough, Mass.), which was described by Hutchinson, M. L., et al., Anatomic Pathology, Vol. 96, No. 3, pp. 300–305(1991), and the CytoRich process system (Hoffman-La Roche Inc., Nutley, N.J.) described in U.S. Pat. No. 5,346,831.

When duplicate smears are available, one smear can be stained according to the conventional Papanicolaou technique and the other smear can be used to detect expression of MN/CA9 antigen. Alternatively, after the cytological examination, a conventional Pap smear sample can be destained to remove Pap stain and then re-stained, for example using immunohistochemical techniques, to detect expression of MN/CA9 antigen.

II. Cytological Dx: The Bethesda System (TBS)

The TBS classification system is used for the preliminary cytological diagnosis of Pap smear cells. The Clinical Laboratory Improvement Act of 1988 mandated a uniform system for reporting Pap smear screening results. The system that was developed pursuant to that Act is known as The Bethesda System (TBS), and has been in effect since 1991, replacing the earlier classification system. There is no accurate way to correlate the two systems, except in the broadest of terms.

The Bethesda System first reports the adequacy of the sample, e.g., if endocervical cells are present, and uses descriptive terms for abnormal results. The System may also describe any benign cellular changes detected on the Pap smear due to fungal, bacterial, protozoal, or viral infection. In addition the results may report if the Pap smear detected reactive cellular changes associated with inflammation, atrophic vaginitis, radiation, or an intrauterine contraceptive device. (IUD).

Pap smears containing atypical cells or cell clusters that do not correspond to benign cellular changes are given a descriptive diagnosis of epithelial cell abnormalities. The descriptive diagnosis of epithelial cell abnormalities is further categorized as squamous or glandular cell abnormalities.

The descriptive diagnosis of squamous cell abnormalities can include: (1) atypical squamous cells of undetermined significance (ASCUS); (2) low-grade squamous intraepithelial lesions (LSIL); or (3) high-grade squamous intraepithelial lesions (HSIL). ASCUS indicates abnormalities that do not fit the criteria for a squamous intraepithelial lesion (SIL), but are nevertheless noteworthy. The ASCUS category may be further qualified with Favor Reactive Process, Changes Associated with Atrophy, or Favor Neoplasia. LSIL includes mild dysplasia and may include changes suggestive of human papilloma virus (HPV). HSIL includes moderate to severe dysplasia, carcinoma in situ, and squamous cell carcinoma.

The descriptive diagnosis of glandular cell abnormalities can include: (1) glandular endometrial cells, which are cytologically benign, in a post-menopausal woman; (2) atypical glandular cells of undetermined significance (AGUS); and (3) pre-invasive or malignant neoplasms such as endocervical, endometrial, extrauterine, or other adenocarcinoma. The AGUS category may be further qualified with Favor Reactive Process, Favor Neoplastic Process and Not Otherwise Specified (NOS).

III. Detection Procedure

Pap smear cells that have been cytologically diagnosed as atypical glandular cells of undetermined significance (AGUS) under the Bethesda System of terminology are subjected to a procedure whereby expression of MN/CA9 antigen is detected.

A. MN/CA9 Antigen

The phrase "MN/CA9 antigen" is herein defined to mean proteins and/or polypeptides encoded by an MN/CA9 gene or fragments thereof. A "polypeptide" is a chain of amino acids covalently bound by peptide linkages and is herein considered to be composed of 50 or less amino acids. A "protein" is herein defined to be a polypeptide composed of more than 50 amino acids. The MN/CA9 gene encodes an MN/CA9 protein of about 48 kDa. MN/CA9 protein is a transmembrane glycoprotein, which may be localized on the cell surface and in the nucleus of HeLa cells and in some human carcinomas. The MN/CA9 protein is expressed in HeLa cells as twin proteins of 54 and 58 kDa, which can form disulfide-linked oligomers. The gene for the MN/CA9 protein includes the nucleotide sequence of SEQ ID NO:1, which encodes the amino acid sequence of SEQ ID NO:2., as described in U.S. Pat. No. 5,387,676, incorporated herein by reference.

It can be appreciated that a protein or polypeptide produced by a neoplastic cell in vivo could be altered in sequence from that produced by a tumor cell in cell culture. Thus, MN/CA9 antigens include proteins and/or polypeptides encoded by MN/CA9 alleles, which have varying amino acid sequences, including without limitation, amino acid substitutions, extensions, deletions, truncations and combinations thereof, that fall within the scope of this invention.

It can also be appreciated that a protein is subject to post-translational modifications, such as proteolytic or degradative processes in vivo; thus, truncated MN/CA9 polypeptides or MN/CA9 proteins that are significantly modified, e.g., by the presence or absence of glycosylated, phosphorylated, adenylated, or myristoylated residues, may also be found in clinical specimens. Accordingly, the phrase "MN/CA9 antigen" is used herein to encompass modified MN/CA9 proteins and/or polypeptides that retain a characterizing fraction of an MN/CA9 protein and/or polypeptide, such as an antigenic determinant or immunoreactive epitope, which binds detectably to an anti-MN/CA9 antibody.

B. Immunohistochemistry

In one embodiment of the present invention, MN/CA9 antigen may be reacted with a binding moiety capable of specifically binding the MN/CA9 protein/polypeptide, thereby producing a binding moiety/MN/CA9 antigen complex. Typically, the specimen is contacted with an antibody that is specific for MN/CA9 antigen under conditions for binding of the antibody to the antigenic site. After contact, the presence or absence of an antibody/antigen complex is determined.

The binding moiety is typically an antibody capable of forming an antibody/MN/CA9 antigen complex, i.e., an anti-MN/CA9 antibody. As used herein, the term "antibody" is understood to mean a binding protein, for example, an immunoglobulin or other protein comprising an immunoglobulin variable region-like binding domain, having the appropriate binding affinity and specificity for MN/CA9 antigen. Methods for generating polyclonal or monoclonal antibodies are well known in the art. The antibody may be from a mammalian source, including human, murine, or a combination thereof. The antibody is preferably IgG, but may be an IgM, IgE, IgA, or the like. Moreover, other useful antibodies having suitable binding domains include antibody fragments, such as Fab, F(ab')$_2$, Fv, and so forth. The antibody fragments may be prepared by conventional techniques, for example, by peptidase digestion of the antibody using papain or pepsin.

Alternatively, antibody fragments may be genetically engineered, preferably from the variable regions of the light and/or heavy chains ($V_H$ and $V_L$), including the hyper variable regions, and still more preferably from the $V_H$ and $V_L$ region. Accordingly, "hybrid" antibodies capable of binding more than one antigen, constant-variable region chimeras, "composite" immunoglobulins with heavy and light chains from different origins, and "altered" antibodies with improved specificity and other characteristics can be prepared by recombinant techniques for use in the present invention.

Monoclonal antibodies are preferred. A murine hybridoma that produces a representative anti-MN/CA9 antibody, the monoclonal antibody M75, was deposited at the American Type Culture Collection [ATCC, Rockville, Md. (USA)] on Sep. 17, 1992, under ATCC Number HB 11128 as disclosed in U.S. Pat. No. 5,387,676 (incorporated herein by reference).

Contact between the antibody and the specimen is generally carried out in an aqueous buffered system. After a period of contact between the specimen and the antibody, the slide is washed with an aqueous buffered solution to remove the unreacted antibody. Next, the binding of antibody to antigen is detected via the use of a labeling system.

To make the determination of the presence of an antigen/antibody(immune) complex, the means for producing a detectable signal is incorporated into the assay system. For example, in direct labeling procedures one may conjugate a primary antibody employed in the assay, e.g., an anti-MN/CA9 antibody, to a label, which is capable of producing a detectable signal. The label may be a chromophore, including fluorescent dyes such as fluorescein, rhodamine, Cy5, and the like; or an enzyme, such as alkaline phosphatase, horseradish peroxidase, glucose oxidase or the like. Alternatively, the primary antibody can be conjugated to a ligand that specifically binds a second binding moiety, wherein the ligand can include haptens, such as DNP or biotin. An indirect labeling procedure may also be used wherein one may contact the washed slide with a second binding moiety, that binds specifically to the primary antibody or to a ligand conjugated to the primary antibody. For example, where a monoclonal antibody derived from a murine source is the primary antibody, a labeled anti-mouse immunoglobulin may be used as a secondary antibody. Alternatively, an avidin containing molecule or an anti-biotin antibody can specifically bind and form a complex with a primary or secondary antibody conjugated to biotin.

Moreover, the primary or secondary binding moieties or their ligands may be linked with a detectable label, such as an enzymatic, fluorescent, radioactive, phosphorescent or colored particle label. The labeled complex may be detected, e.g., by microscopic examination or with the aid of an image detector.

C. Amplification and In Situ Hybridization

In another embodiment of the present invention, MN/CA9 expression can be determined using in situ cytohybridization to selectively detect a target RNA molecule encoding an MN/CA9 protein/polypeptide. The target mRNA molecule may be amplified and detected, for example, with primers and hybridization probes capable of hybridizing specifically with at least a portion of the mRNA molecule encoding the MN/CA9 protein/polypeptide or its complementary sequences. Preferably, the primers and/or hybridization probes are oligonucleotides substantially complementary or identical to portions of SEQ ID NO:1. Most preferably, the probes are capable of hybridizing with sequences complementary to SEQ ID NO:1 under moderate to stringent hybridization conditions.

IV. Distribution of MN/CA9 Antigen and Dx

The next step of the method is observing the distribution of MN/CA9 antigen expressed on atypical and/or normal cells of the AGUS cytologically diagnosed Pap smear.

Morphologically normal reserve and columnar cells, including metaplastic squamous cells, constitute the cell population that we define as normal endocervical cells (ECs). Any cell clusters that morphologically deviate from normal squamous cells, endocervical reserve cells, or columnar cells are considered atypical cell clusters. The nuclei of atypical cells are, in general, 3 to 5 times larger than normal ECs and exhibit significant hyperchromasia with an increased nuclear/cytoplasmic ratio. Atypical cells may be derived from atypical squamous metaplasia, atypical reserve cell proliferation, and endocervical glandular atypia.

The distribution of MN/CA9 antigen expression may fall within one or more general patterns. A negative MN/CA9 expression pattern exists either when no label is observed or two or less normal endocervical cells are detectably labeled. On the other hand, a positive MN/CA9 expression pattern is present when detectable label is observed in any atypical cell cluster or in more than two normal endocervical cell clusters. A diffuse staining pattern is when the majority of the atypical cells/cell clusters or more than 100 normal endocervical cells/cell clusters in each smear exhibit strong MN/CA9 expression. In addition, a focal pattern of staining is observed when only isolated endocervical cell clusters and/or atypical cells are positive.

The method of the present invention lowers the level of false negative results in Pap smear cells previously diagnosed as AGUS. The precursor to cervical cancer is dysplasia, also known in the art as cervical intraepithelial neoplasia (CIN) or squamous intraepithelial lesions (SIL). Cells are diagnosed as AGUS when atypical cells are observed, putatively of glandular origin, which the cytologist does not consider to be dysplasia. In the method of the present invention, false negative results are avoided because significant or serious cancerous or pre-cancerous lesions are associated with MN/CA9 antigen detection on atypical cells of AGUS-diagnosed Pap smear specimens. The significant lesions can include adenocarcinoma, invasive carcinoma (CA), and high grade SIL (HSIL). Expression of MN/CA9 antigen on atypical cells is occasionally associated with low grade SIL (LSIL), however this "false positive" result may forewarn of lesions that will progress to HSIL.

Preferred embodiments of the present invention include two particular MN/CA9 antigen staining patterns, typically found on atypical cells, that are always diagnostic of Pap smears obtained from patients having a significant or serious lesions associated with cervical cancer or its precursor.

In one preferred embodiment of the present invention, the Pap smear cells exhibit a pattern of MN/CA9 expression described herein as focally columnar or as a honeycomb configuration. Examples of the honeycomb pattern can be found in FIG. 2 (panel I), FIG. 6 (panel F) and FIG. 7 (panel F). The honeycomb configuration on atypical cells and clusters in a diffuse pattern, is a characteristic of Pap smears obtained from patients with adenocarcinoma (AIS) or invasive adenocarcinoma.

Figure 2:
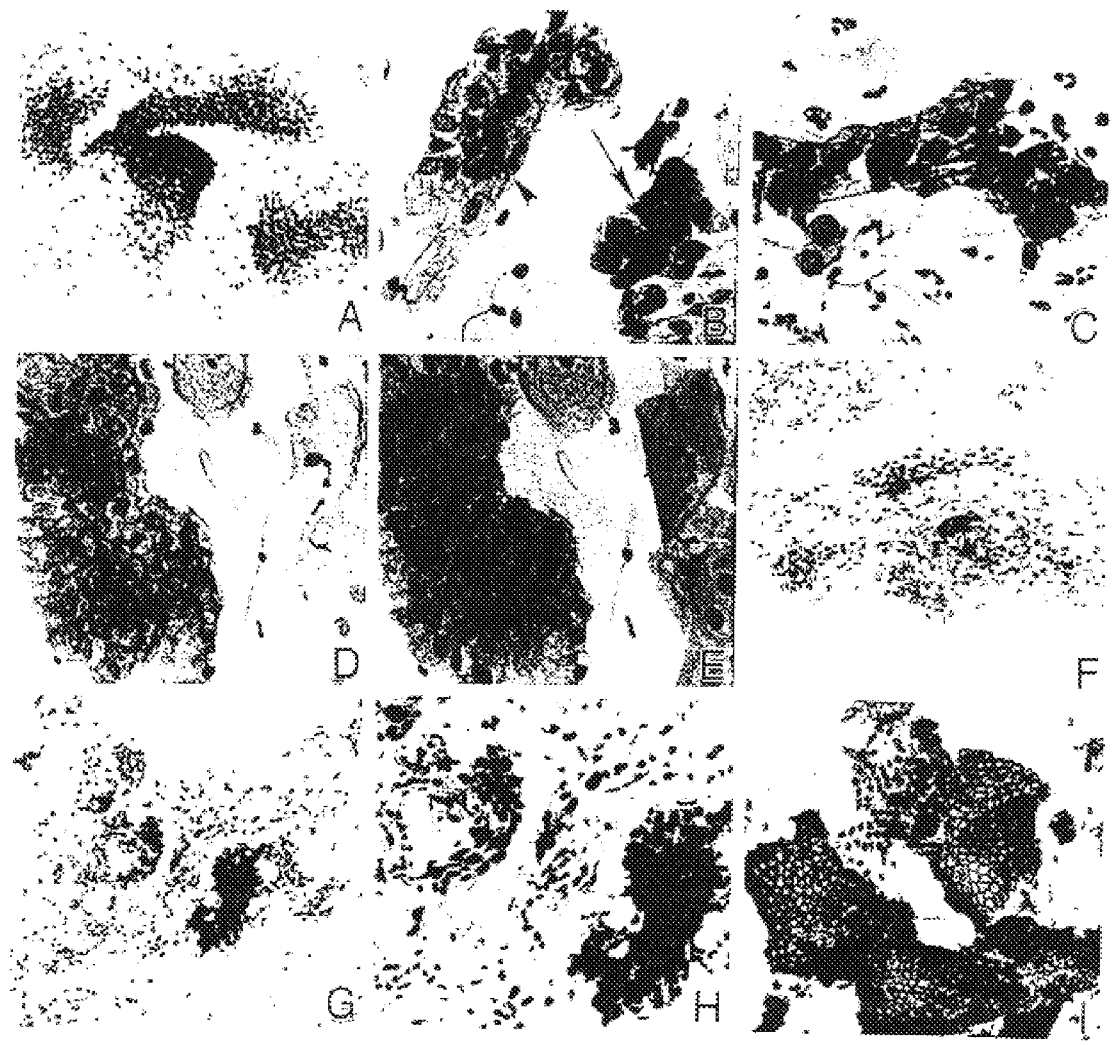
FIG. 2 shows staining patterns of MN/CA9 immunoreactivity in AGUS Pap smears: Panel A is a smear that shows no immunostaining; Panel B shows positive immunostaining in both atypical cells (arrow) and normal ECs (arrowhead), Panel C shows MN/CA9 positive atypical cells only, Panel D is an example of immunoreactivity of normal ECs only, with the corresponding Pap stain in panel E, moreover the pattern of immunoreactivity may be focal (panel F) or diffuse (panel G), and the morphology of the immunostained cells may be tight clusters (panel H) or honeycomb configuration (panel I) (Magnification: A, F and G 100×; H and I 200×; B, C, D and E, 400×)
Figure 5:
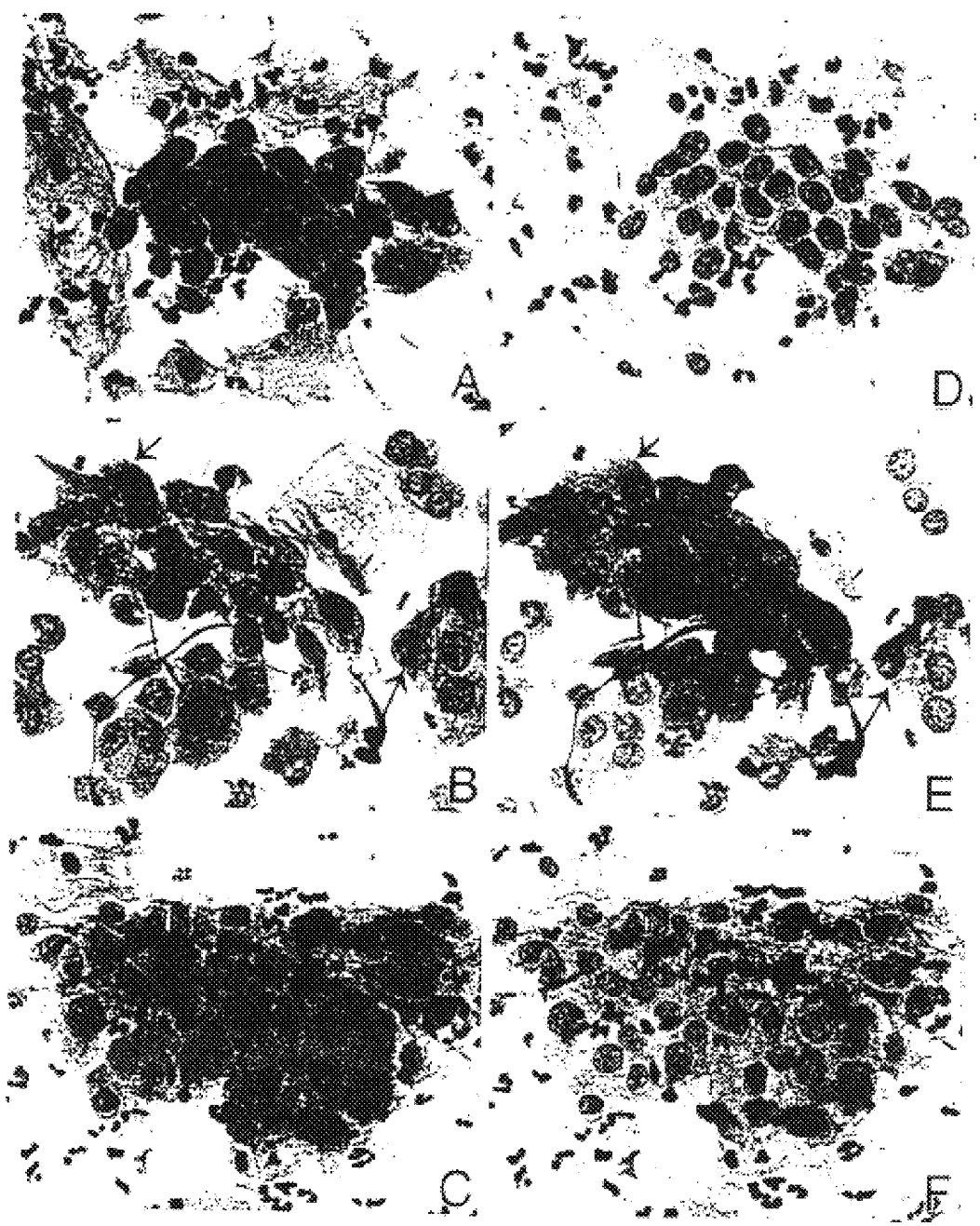
FIG. 5 shows cytologic features of atypical cell clusters in AGUS-favor reactive Pap smears, such as enlarged nuclear size with minimal cellular overlap and mild degree of nuclear pleomorphism (panels A, B and C), and the same cell clusters, destained and then immunostained to detect MN/CA9 expression provide examples where no immunoreactivity correlated with no histological lesion (panel D), and strong (panel E) and weak immunoreactivity (panel F) was associated with histologic diagnoses of HSIL: note that the ciliated cells pointed to in panel E are MN/CA9 negative (Magnification: 400×)
Figure 6:
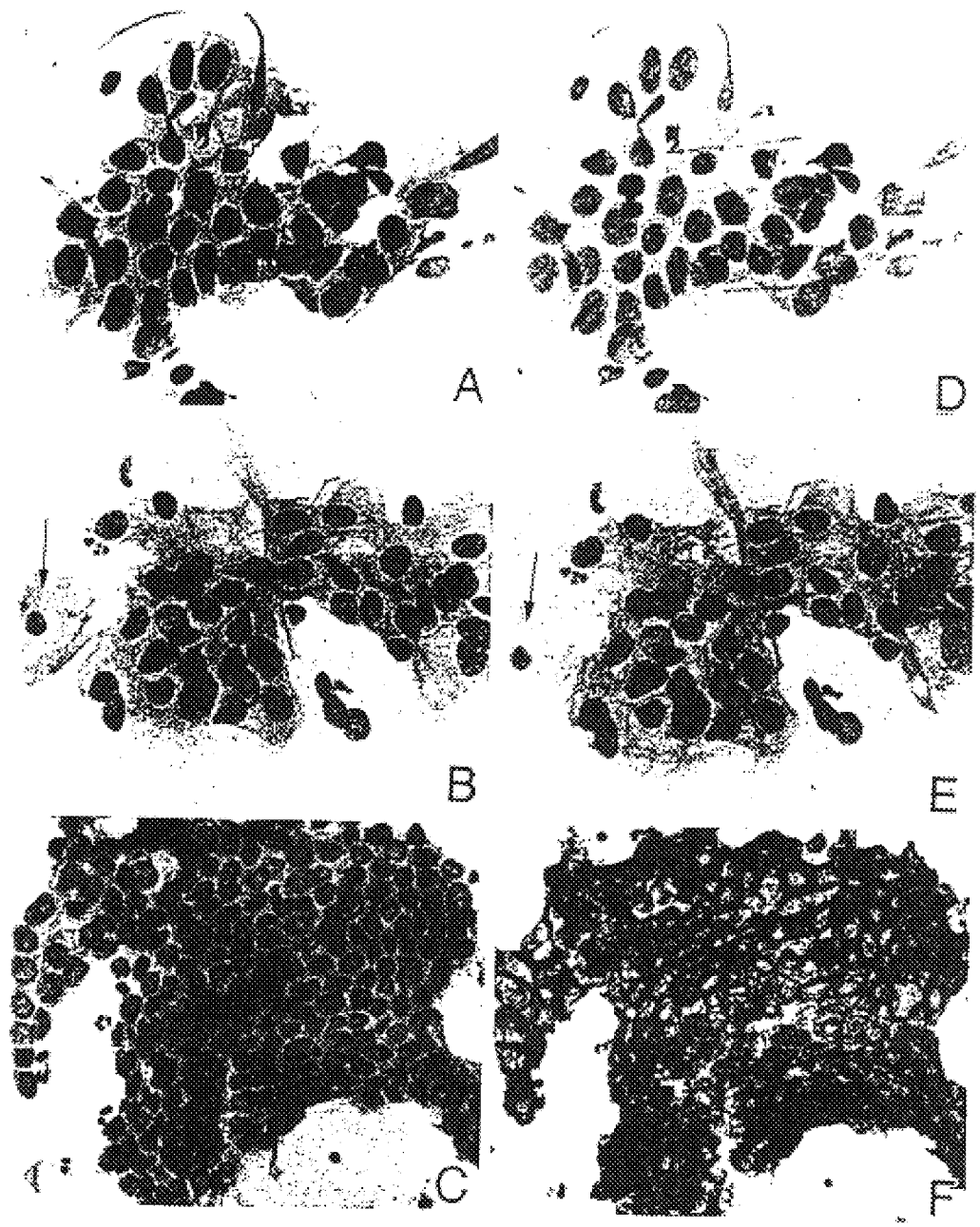
FIG. 6 shows cytologic features of atypical cell clusters in AGUS-NOS Pap smears (panels A, B and C), such as nuclei 3× larger than the nuclei of the adjacent intermediate cells (arrow), and increased cellular overlap and nuclear hyperchromasia, however corresponding MN/CA9 immunostains of the same specimens demonstrate a negative immunostain in Panel D that corresponds with a follow-up biopsy that was negative, a positive immunostain in panel E corresponding with a histologic diagnosis of HSIL, and a characteristic honeycomb pattern of immunostaining in panel F that corresponds with a follow-up biopsy diagnosed as adenocarcinoma. (Magnification: 400×)

In another preferred embodiment of the present invention, the Pap smear cells exhibit a pattern of MN/CA9 expression on atypical cells that are arranged in tight clusters (for reference see FIG. 2, panels B, C, F, G, and H; FIG. 5, panels E and F; FIG. 6, panel E; and FIG. 7, panel E). The pattern of staining of atypical cells in tight clusters can be diffuse or focal (see, e.g., FIG. 2, panels F and G) and is usually a characteristic of Pap smear cells from patients with high grade SIL (HSIL).

In yet another embodiment of the present invention low grade lesions are distinguishable from more serious lesions. Such low grade lesions are associated with another staining pattern, wherein expression of MN/CA9 antigen is not detected on atypical cells, but is restricted to normal cells. Staining that detects the presence of MN/CA9 antigen only on normal ECs is diagnostic of Pap smears obtained from patients having less serious low grade lesions, including low grade SIL (LSIL) and atypia.

Table 1 compares the present study with follow-up studies conducted by several other laboratories in those cases diagnosed as endocervical atypia. The cumulative results, as shown in Table 1, indicate that approximately 40% of AGUS cases represent high grade SIL, adenocarcinoma in situ (AIS), or carcinoma, and correspondingly 60% represent benign or insignificant lesions.

TABLE 1

Follow-up Histologic Diagnosis of Cases with Cytologic Diagnosis of Atypical Glandular Cells (AGUS) in Routine Pap Smears

| Follow-up diagnosis | Reference | | | | | | | |
| --- | --- | --- | --- | --- | --- | --- | --- | --- |
| | Wilbur et al | Goff et al | Lee et al | Bose et al | Taylor et al | Kenney et al | This study | Average |
| Benign/atypia | 46* | 40 | 42 | 20 | 64 | 81 | 19 | 44 |
| LSIL | 13 | 24 | 0 | 37 | 17 | 4 | 31 | 18 |
| HSIL | 32 | 30 | 44 | 41 | 20 | 5 | 39 | 30 |
| AIS/Adenoca. | 9 | 13 | 14 | 0 | 0 | 10 | 11 | 8 |
| Significant lesions** | 41 | 43 | 58 | 41 | 20 | 15 | 50 | 38 |
| Total No. of cases | 225 | 56 | 74 | 44 | 77 | 30 | 245 | |

*Data presented as percentages.
**Significant Lesions = HSIL and AIS/CA

Finally, preferred versions of the present invention include a step wherein the absence of any pattern of MN/CA9 expression described above generally correlates with a benign condition. Consequently, a negative staining pattern, where neither normal nor atypical cells exhibit staining for MN/CA9 antigen, is diagnostic of a benign condition.

The present invention provides an improved method for diagnosing the presence of significant and low grade lesions associated with cervical cancer and its precursors. The method overcomes the problems of uncertainty and/or false negative results in Pap smear specimens, previously categorized as atypical glandular cells of undetermined significance (AGUS). Despite the absence of readily ascertainable dysplasia on the Pap smear specimen, the method can distinguish less serious lesions from significant cancerous or pre-cancerous lesions in the cervix. Moreover, the absence of MN/CA9 expression is a reliable indicator of a benign condition.

Although the present invention has been described in considerable detail with reference to certain preferred versions thereof, other versions are possible. For example, it is contemplated that the screening assays of the present invention may be automated, thereby facilitating the screening of a large number of specimens at the same time. Therefore, the spirit and scope of the appended claims should not be limited to the description of the preferred versions described herein.

EXAMPLES

A total of 245 Pap smears with individual cytologic diagnoses of AGUS, with or without SIL, were studied. Corresponding histologic examination of biopsy material was conducted in each case. We found that MN/CA9 immunoreactivity was seen in all cases where atypical and neoplastic cervical tissues were diagnosed. In contrast, Pap smears of normal cervices with a cytologic diagnosis of AGUS were MN/CA9 negative. Importantly, high levels of the MN/CA9 protein expression were seen in all cases of AIS and invasive adenocarcinoma.

Materials and Methods

Tissue Specimens: Individual Pap smears from 557 patients with a cytologic diagnosis of AGUS with or without SIL (incidence: 0.3%) were retrieved from 185,414 Pap smears examined by a private cytologic laboratory in Orange County, Southern California, between July, 1994 to September, 1998. The follow-up histologic confirmation was identified in 251 Pap smears (follow-up rate: 43%). Among these, six cases were excluded due to insufficient material in the endocervical curettage (n=3), endometrial curettage only (n=2), and air-dried smear (n=1). Thus, the total number of Pap smears included in the study was 245. The median age of the patients included in the study was 39 (range was 20–81 years). All of the Pap smears were collected by a cytobrush and a wooden spatula. The sources of tissue sections of the cervices were from colposcopic-directed cervical biopsies, endocervical curettage, cervical conization or hysterectomy.

Cytology

The Pap smears were screened by 6 cytotechnicians and reviewed by 8 pathologists, including three board certified cytopathologists. The TBS classification was used in the study and cytologic diagnosis of AGUS was further classified as AGUS-favor reactive, AGUS-favor neoplastic, and AGUS-not otherwise specified (AGUS-NOS). The Pap smears were not reviewed for diagnostic stringency; thus the results are concordant with the actual cytologic screening in a private practice situation. The cytologic and histologic data were correlated. The MN/CA9 immunoreactivity was interpreted in a blinded fashion and the results were then correlated with the histologic data. Only in those cases where there was a discrepancy between the original histologic diagnosis and MN/CA9 immunoreactivity were the histologic sections reviewed with knowledge of the results of MN/CA9 immunostaining.

Immunohistochemical Studies

The mouse monoclonal antibody used to detect the MN/CA9 protein has been described previously (Pastorek et al., 1994). The antibody recognizes the antigen in formalin fixed, paraffin embedded sections and archived Pap smears (Liao et al., 1994; and Liao et al., 1996). Immunohistochemical staining of tissue sections and decolorized Pap smears with the anti-MN/CA9 Mab (MN75) was done using a peroxidase technique described previously (Hsu S M, Raine L, Fanger H. Use of avidin-biotin peroxidase complex (ABC) in immunoperoxidase techniques: a comparison between ABC and unlabeled antibody (PAP) procedures. J. Histochem. Cytochem., 1981. 29:577–580). Known positive and negative tissue specimens were included in each run. Briefly, the smears were decolorized with 1% acid alcohol and rinsed with distilled water. Five micron sections of paraffin-embedded tissues were deparaffinized. The endogenous peroxidase was blocked by incubating the slides in a solution of 3.0% hydrogen peroxide in methanol for 10 min. The slides were then incubated with appropriate blocking serum (5% normal horse serum in PBS), followed by incubation with purified ascites fluid-derived primary antibody MN75 (1:10,000 dilution in PBS containing 0.1% BSA) for 60 minutes. The secondary biotinylated horse antimouse immunoglobulin G antibody (1:200 dilution in PBS) was then added for 30 min., followed by incubation with avidin-biotin peroxidase complex (ABC Elite) for 30 min. (Vector Laboratories, Burlingame, Calif.). Diaminobenzidine tetrahydrochloride was used as chromagen (Sigma Chemical Co., St. Louis, Mo.). After treatment, the sections were washed with distilled $H_2O$, counterstained with hematoxylin, and mounted with Permount.

Immunohistochemical analysis

The specificity of staining was defined by the presence of a brown reaction product predominantly on the plasma membrane. The intensity of the staining was subjectively defined by using a two scale system; namely weak (+) and strong (++ to +++). Very weak staining of the cytoplasm, detectable only at a high-power magnification, was considered as negative because of the lack of specificity (Liao et al., 1996). All of the cells and/or cell clusters that stained, either weakly or strongly, were evaluated under the high-power magnification. Any MN/CA9 immunoreactive cells in cell clusters that morphologically deviated from normal squamous cell, endocervical reserve cell or columnar cell were considered as atypical cell clusters. The nuclei of those atypical cells were, in general, 3 to 5 times larger than normal endocervical cells (ECs) and exhibited significant hyperchromasia with an increased nuclear/cytoplasmic ratio. The numbers of positive cells or cell clusters in each smear were counted under 4x scanning power. Diffuse MN/CA9 immunoreactivity was defined as when more than 50% of the atypical cells/cell clusters or more than 100 normal endocervical cells/cell clusters in each smear exhibited strong (++/+++) MN/CA9 immunoreactivity. The smear was scored as positive when brown staining was identified in any atypical cell cluster or in more than two normal endocervical cell clusters, and negative when no brown reaction was seen or staining was limited to two or less normal endocervical cell Clusters in each smear.

Example 1

Histology

The tissue sections of the cervix from each case were reviewed and interpreted as benign, atypia, cervical intraepithelial neoplasia (CIN), or AIS/Carcinoma (AIS/CA). The criteria used for diagnoses of glandular atypia/neoplasia and CIN are those defined by Crum & Kurman (Crum C P, Cibas E S, Lee K R. Criteria for grading squamous intraepithelial lesions. In: Pathology of Early Cervical Neoplasia, New York Churchill Living stone, 1997. 47–91; and Kurman R J, Norris H J, Wilkinson E. Tumors of the cervix, vagina, and vulva. In: Atlas of Tumor Pathology, 3rd series, fasc. 4, Armed Forces Institute of Pathology, 1992. 37–139). Representative examples are shown in FIG. 1. The benign category included normal cervix with or without inflammation (panel A). The diagnosis of atypia included atypical squamous metaplasia/atypical reserve cell proliferation and endocervical glandular atypia (panels B and C). A two scale system was used for the diagnosis of CIN, namely low grade (Condyloma/CIN I) (panel D) and high grade (CIN II and CIN III) (panel E). An example of AIS is shown in panel F.

Correlation Between Cytology and Histology

The comparative analysis between the various categories of AGUS Pap smears and the histologic diagnoses of the cervical specimens is outlined in table 2.

TABLE 2

Biopsy Follow-Up of Patients with Cytologic Diagnosis of AGUS Cytologic Diagnosis

| | AGUS-ALL CATEGORIES | | AGUS-FAVOR REACTIVE N - 29 | | AGUS-NOS N = 157 | | AGUS-FAVOR NEOPLASTIC N = 59 | |
|---|---|---|---|---|---|---|---|---|
| Histologic | N = 245 | | Without SIL | With SIL | Without SIL | With SIL | Without SIL | With SIL |
| Diagnosis | No. | (%) | n = 28 | n = 1 | n = 137 | n = 20 | N = 51 | n = 8 |
| Benign | 34 | (14) | 13 | 0 | 20 | 0 | 1 | 0 |
| Atypia* | 12 | (5) | 3 | 0 | 8 | 0 | 1 | 0 |
| LSIL | 76 | (31) | 9 | 1 | 55 | 2 | 7 | 2 |
| HSIL | 95 | (39) | 1 | 0 | 49 | 18 | 22 | 5 |
| Endometrial Adenoca. | 3 | (1) | 0 | 0 | 0 | 0 | 3 | 0 |
| AIS** | 25 | (10) | 2 | 0 | 5 | 0 | 17 | 1 |

*Atypical squamous metaplasia, atypical reserve cell proliferation, or glandular atypia.
**Coexisting early stromal invasion was seen in 3 cases.

Of the 245 cases studied, 29 (12%) of the Pap smears were diagnosed as AGUS-favor reactive, 157 (64%) as AGUS-NOS, and 59 (24%) as AGUS-favor neoplastic. Coexisting cytologic diagnosis of SIL was found in Pap smears of one AGUS-favor reactive, 20 AGUS-NOS and 8 AGUS-favor neoplastic.

Biopsy follow-up showed thirty four (14%) of the cervices had no obvious abnormalities. The corresponding Pap smears were 13 specimens diagnosed as AGUS-favor reactive, 20 as AGUS NOS and one specimen diagnosed as AGUS-favor neoplastic.

Twelve (5%) of the cervical specimens received a histologic diagnosis of atypia. The cytologic diagnoses were: 3 AGUS-favor reactive, 8 AGUS-NOS, and 1 AGUS-favor neoplastic.

A significant fraction of the histologic diagnoses were LSIL (76 cases) or HSIL (95 cases). In the cases of LSIL diagnosis the corresponding cytologic diagnoses were: 10 AGUS-favor reactive, 57 AGUS-NOS, and 9 AGUS-favor neoplastic. A similar broad distribution of cytologic diagnoses was seen in the HSIL cohort. There were 1 AGUS-favor reactive, 67 AGUS-NOS, and 27 AGUS-favor neoplastic.

In the most serious lesion category, that of AIS/CA, there were 28 cases (11%), of which three were endometrial adenocarcinomas. The corresponding cytologic diagnoses were: 2 AGUS-favor reactive, 5 AGUS-NOS, and 21 AGUS-favor neoplastic.

Thus, our study indicated that 50% of the AGUS Pap smears had significant lesions (HSIL and AISICA) in the follow-up biopsies. Although the majority (81%) of AGUS-favor neoplastic Pap smears were histologically confirmed to be HSIL or AIS/CA, only 46% of the AGUS-NOS Pap smears had significant lesions found in the cervices. Thus, these diagnoses clearly reflect the quandary facing the clinician. The diagnosis of AGUS-NOS was easily the most frequently used of the cytologic diagnostic categories of AGUS and was not very helpful in predicting clinical outcome.

MN/CA9 Immunoreactivity in Pap Smears

In normal Pap smears the exfoliative endocervical cells/cell clusters and endometrial cells from the lower uterine segment are consistently MN/CA9 negative (data not shown). In the AGUS Pap smears we found a relatively complex pattern of cytologic morphology/immunoreactivity combinations. These are illustrated in FIG. 2 and serve as a framework for succeeding interpretations in the study. Cytologic criteria for atypical glandular cells, delineated in the TBS classification, were used in the interpretation (National Cancer Institute Workshop. The revised Bethesda System for reporting cervical/vaginal cytologic diagnosis: report of the 1991 Bethesda Workshop. JAMA, 1992. 267:1892; and Kurman et al., 1994). Panel A shows an AGUS Pap smear that exhibits no MN/CA9 immunoreactivity. In smears where positive immunostaining is seen there are two broad categories: those where atypical cells, with or without normal ECs, are positive and those where normal ECs only stain (panels B–D). In those smears that do exhibit positive immunostaining, variations in intensity of stain are encountered. Panel B illustrates clusters of atypical cells that are strongly positive (arrow) and normal ECs that are weakly positive (arrowhead). The pattern of immunostaining may also vary. Panel F shows an example of focal staining and panel G shows an example of diffuse immunoreactivity. In those Pap smears where atypical cells were stained, there are morphological variations. Some of the stained atypical cells are arranged in tight cell clusters (panel H), where in other smears focally columnar or honey-comb configurations were observed (panel 1).

Correlation Between MN/CA9 Immunostaining and Histologic Diagnosis

Figure 3:
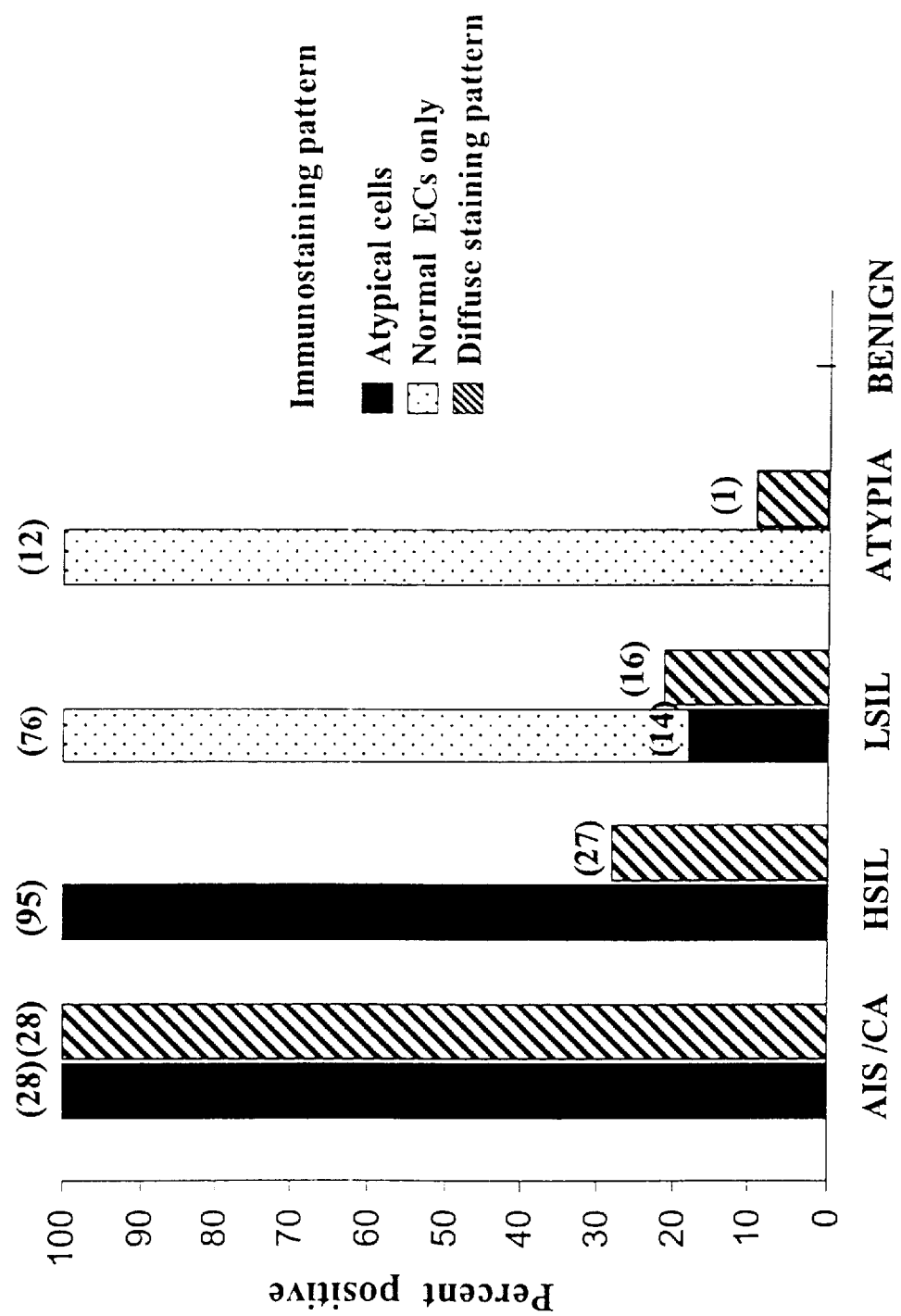
FIG. 3 shows distributions of MN/CA9 immunostaining of AGUS Pap smears and their correlation with histologic diagnosis.

The distribution of immunostaining patterns described above, and their correlation with histologic diagnosis, is illustrated in FIG. 3. It is immediately apparent that all specimens with histologic diagnoses ranging from atypia to AIS/CA are positive for MN/CA9 expression. Conversely, all cases of benign cervices had MN/CA9 negative Pap smears.

There was an interesting correlation between the degree of dysplasia diagnosed histologically and the morphology of the MN/CA9 positive cells in the corresponding Pap smears. Those specimens with a histologic diagnosis of AIS/CA or HSIL exhibited, in all cases, immunostaining of atypical cells±normal ECs in the corresponding Pap smears. Moreover, immunoreactive atypical cells in cases of AIS/CA always exhibited focally columnar or honeycomb features, with a diffuse staining pattern. Conversely, in cases of HSIL, the MN/CA9 positive atypical cells usually were arranged in tight clusters (for reference see FIG. 2, panels B, C, H and I), and only a fraction of the cases (28%) exhibited a diffuse immunostaining pattern. In the cases of diagnoses of LSIL, 14/76 showed a similar pattern, whereas the remainder exhibited staining of normal ECs only (for reference see FIG. 2, panel D). The number of cases with a histologic diagnosis of atypia is small (n=12) but all of them exhibited immunostaining of normal ECs only. Finally, all of the benign cases were MN/CA9 negative.

What is immediately apparent from these data is that in the vast majority of cases where atypical cells exhibit MN/CA9, the presence of a significant lesion (HSIL and AIS/CA) is indicated. The picture is less clear for low grade lesions. Whereas, a fraction of LSIL cases (14/76) do, indeed, show immunostaining of atypical cells, the remainder showed only normal ECs expressing the antigen. This latter feature is also seen in all cases of atypia (n=12). Thus, from these criteria it is not possible to distinguish with confidence these latter two categories of histologic diagnosis on the basis of MN/CA9 immunoreactivity.

Statistical Analysis

The immunopositive smears were subjected to a true diagnosis analysis (Dunn G, Everitt B. Clinical problems and statistical solutions. In Clinical Biostatistics, New York Halstead Press 1995; 1–32). In this analysis the association of immunostained atypical cells with a significant lesion in the corresponding biopsy is considered to have positive predictive value. Correspondingly, the correlation of immunostained normal ECs only with a significant lesion is considered to have a negative predictive value. The analysis is presented in Table 3. Clearly, sensitivity, specificity, and positive predictive values are excellent.

TABLE 3

True Diagnosis Analysis of Immunopositive Smears

| Test result | True diagnosis | |
|---|---|---|
| | HSIL/AIS/CA | LSIL/Atpia |
| Atypical cell Positive | 123 | 14 |
| Normal cell only Positive | 0 | 74 |

Sensitivity=123/123=1.00 (100%)
Specificity=74/88=0.84 (84%)
Positive Predictive Value=123/137=0.90 (90%)
Negative Predictive Value=74/74=1.00 (100%)

Example 2

The categories of AGUS Diagnosis and Their Patterns of Immunostaining

Figure 4:
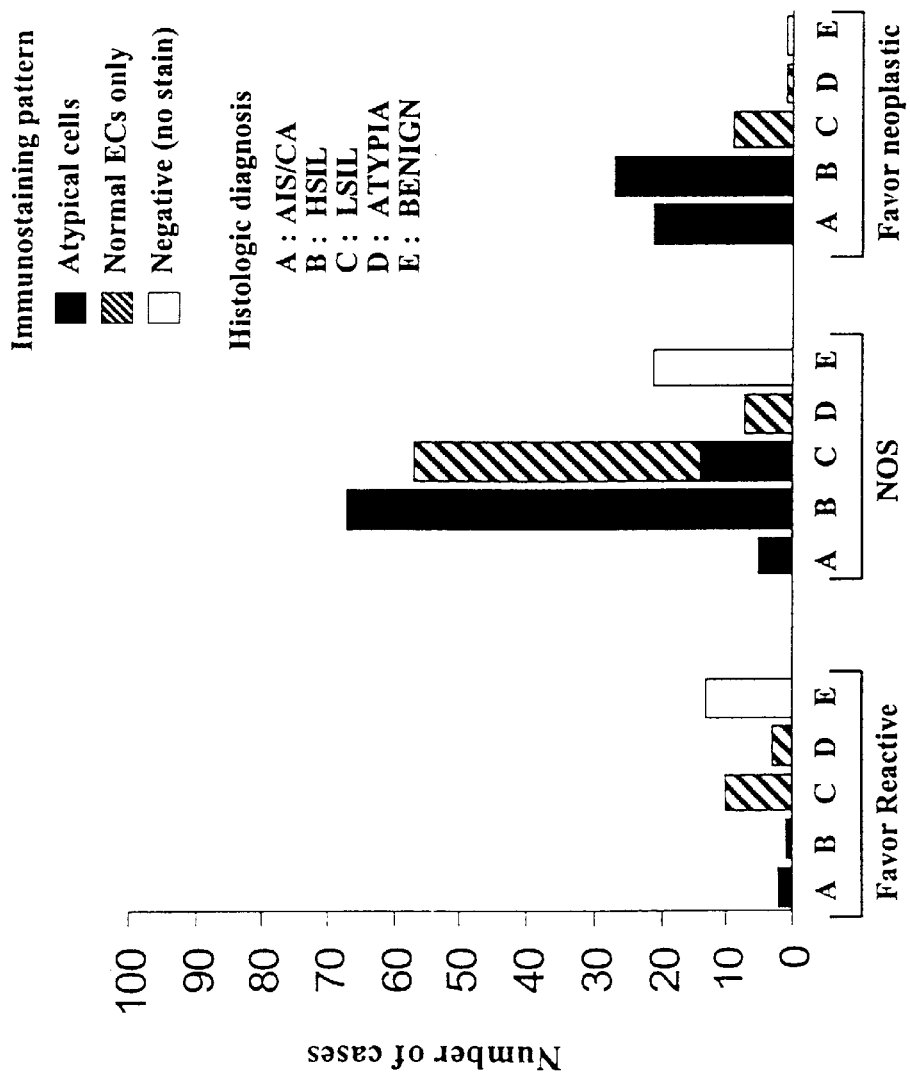
FIG. 4 shows the distribution of MN/CA9 immunostaining of AGUS Pap smears in the three categories: favor reactive, not otherwise specified (NOS), and favor neoplastic, and their correlation with histologic diagnosis.

It is clear from the preceding data that high grade lesions are predicted on the basis of MN/CA9 immunostaining of atypical cells in the relevant Pap smears that have received a general diagnosis of AGUS. FIG. 4 shows how predictive AGUS diagnoses ( i.e. AGUS-favor reactive, AGUS-NOS and AGUS-favor neoplastic) were when compared to their respective patterns of MN/CA9 immunostaining.

Agus-Favor Reactive

A total of 29 cases were diagnosed in this category. In keeping with the cytologic diagnoses, follow up biopsies were benign in 45% (n=13). All of these were MN/CA9 negative. Three cases of atypia and 10 cases of LSIL were diagnosed. All of these showed MN/CA9 immunostaining of normal ECs only. There were also 1 case of HSIL and 2 cases of AIS. All were MN/CA9 positive, with atypical cells staining. Importantly, the few cases where significant lesions were seen were predicted by MN/CA9 immunostaining of atypical cells.

Examples of the Pap staining and immunostaining are shown in FIG. 5. All of the atypical cell clusters in panels A, B, and C show minimal cellular overlap and nuclear pleomorphism, with a mild degree of hyperchromasia. In panel B the atypical cells are associated with ciliated metaplastic cells (arrow). However, when there was MN/CA9 immunostaining of the cells, including ciliated cell clusters (panels E and F), high grade lesions (HSIL) were found in the cervices. Conversely, no dysplastic tissue was identified when no immunostaining was seen (panel D).

Agus-Nos (Not Otherwise Specified)

This was the largest category of the AGUS diagnoses (n=157). The histologic diagnoses clearly indicate the clinical problem with this area. The full range of benign, low grade and high grade lesions were found, with significant numbers in each category (Table 2). Once again, all high grade lesions showed MN/CA9 immunostaining of atypical cells in Pap smears. In the cases of LSIL, only 14/76 showed this pattern; immunostaining, of normal ECs only was seen in the remainder, as was seen in the cases of the histologic diagnoses of atypia. Thus, in those cases where significant lesions (HSIL and AIS) were present, they were readily diagnosed on the basis of MN/CA9 positivity. Importantly, they represented 46% of the total in this category of AGUS-NOS.

Examples of the Pap staining and immunostaining are shown in FIG. 6. All of the atypical cells in panels A, B and C show cellular overlap, moderate nuclear pleomorphism and slightly increased nuclear/cytoplasmic ratio. Again, HSIL (panel E) and AIS (panel F) were histologically identified only in those cases where atypical cells stained positive. No dysplastic lesion was observed in those cases in which no MN/CA9 immunostaining was detected (panel D).

Agus-Favor Neoplastic

The majority of histologic diagnoses in this category confirmed the presence of significant lesions (HSIL, AIS/CA). As illustrated in Table 2, there were 27 (46%) HSIL and 21 (36%) AIS/CA cases. All showed MN/CA9 immunostaining of atypical cells. Those cases diagnosed as LSIL and atypia (n=9 and n=1, respectively) showed positive staining of normal ECs only. Once again the MN/CA9 immunostaining pattern accurately predicted the presence of significant lesions.

Figure 7:
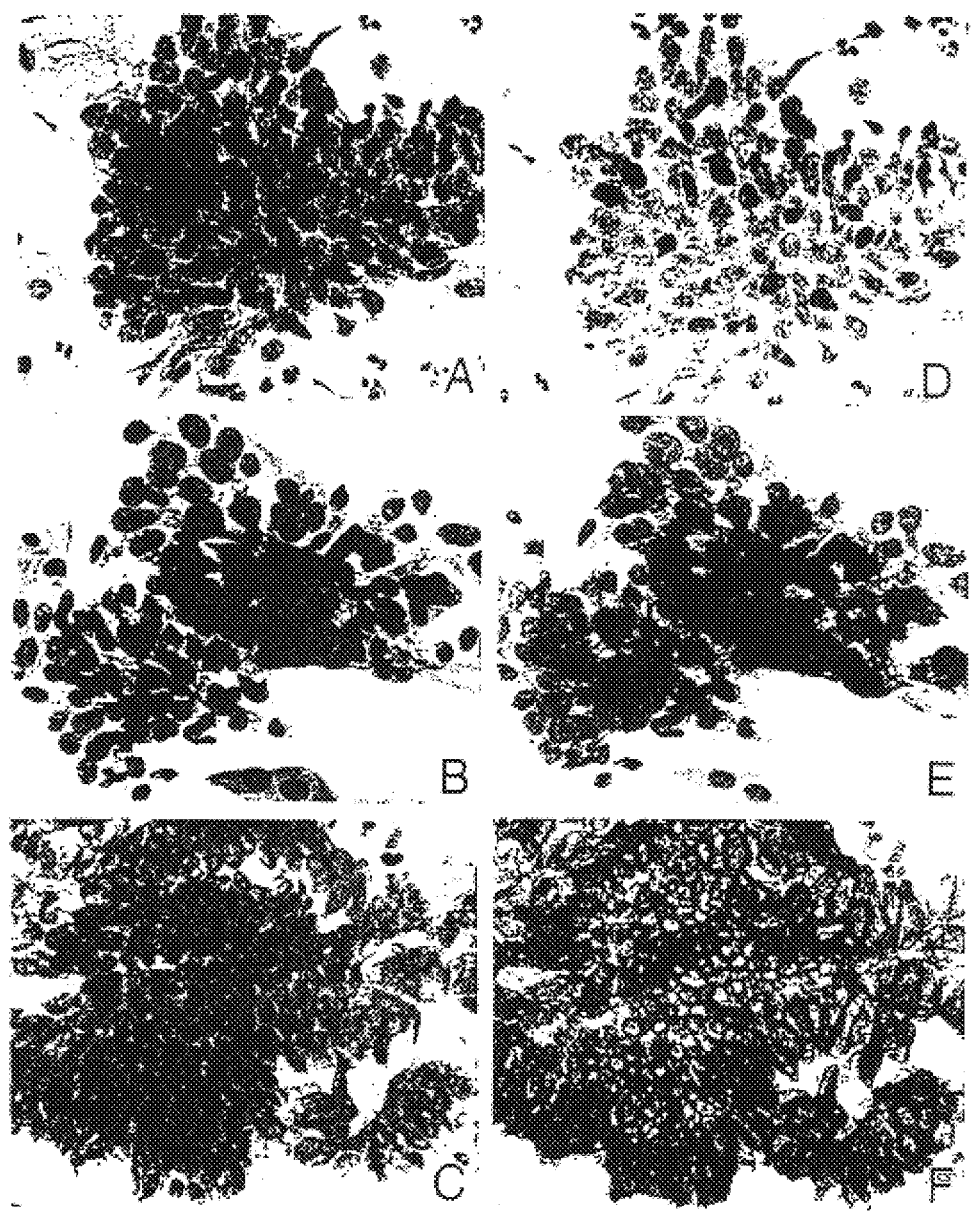
FIG. 7 shows cytologic features of atypical cell clusters in AGUS-favor neoplastic Pap smears, such as significant cellular overlap, nuclear pleomorphism and hyperchromasia (panels A, B and C) and the corresponding MN/CA9 immunostains show examples where a negative immunostain (panel D) corresponds with a follow-up biopsy that is benign, a positive immunostain (panel E) corresponds with a histologic diagnosis of HSIL, and stained cells, which exhibit honeycomb and columnar features (panel F), corresponds with a follow-up biopsy diagnosed as AIS (Magnification: 400×).

Examples of the Pap staining and immunostaining are shown in FIG. 7. All of the atypical cell clusters in panels A, B and C show cellular overlap, marked nuclear pleomorphism, hyperchromasia and increased nuclear/cytoplasmic ratio. HSIL and AIS were observed in the corresponding cervices of those Pap smears where MN/CA9 immunostaining was seen in the atypical cell clusters (panels E and F). Benign histology was seen in the MN/CA9 negative Pap smear (panel D).

Discussion

In the present invention, we have uncovered a clear association between MN/CA9 immunostaining of atypical cells±normal ECs in AGUS Pap smears and the presence of significant lesions in the cervix, whether they be HSIL or AIS/CA (FIG. 3). Similarly, we have uncovered a clear correlation between the lack of MN/CA9 immunostaining and the absence of lesions in the cervix. However, the MN/CA9 immunostaining pattern does not discriminate between LSIL and atypia. In all cases of atypia and 82% (n=62) of LSIL cases, immunostaining of normal ECs only was observed. The remainder of the LSIL cases showed staining of atypical±normal ECs. This small number (n=14) of LSIL cases may represent a small percentage of false positives (in the sense that staining of atypical cells is diagnostic of the presence of significant lesions in the cervix) or may be a prognostic indication that these lesions will progress to HSIL. In addition, the immunostaining pattern seen in AIS cases is always diffuse and the stained cell clusters exhibit columnar or honeycomb configurations. This is in contrast to cases of HSIL, where the cells are arranged in tight clusters, and in the majority of cases they exhibit a focal pattern of immunostaining. Therefore, on this basis of the difference in morphologies of the stained cell clusters and their immunostaining patterns one is able to discriminate between AIS and HSIL in the AGUS Pap smear diagnoses. This has clear and significant clinical implications.

The value of the diagnostic procedures of this invention as an adjunct to cytologic diagnosis is particularly apparent when the AGUS smears are clustered into the three subcategories of AGUS-favor reactive, AGUS-NOS. and AGUS-favor neoplastic (FIG. 4). As expected, the majority of AGUS-favor neoplastic diagnoses correlated with the presence of significant lesions. All of these also showed MN/CA9 immunostaining of atypical cells. The cases of LSIL and atypia (total n=12) showed positive staining of normal ECs only. The category of AGUS-NOS showed the broadest range of lesions in follow-up biopsies. Again, MN/CA9 immunostaining of atypical cells predicted all of the cases where significant lesions were found. A small fraction (n=14) of "false positives" were found here, which are LSIL cases where atypical cells are MN/CA9 positive. It is interesting that this "false positive" staining pattern is found only in the AGUS NOS category and may, as discussed above, be prognostic of a lesion that is destined to progress. In the AGUS-favor reactive category relatively few (n=3) had significant lesions. All were correctly diagnosed by MN/CA9 immunostaining pattern and no false positives were noted.

These data demonstrate that in the context of the present invention, MN/CA9 antigen expression in atypical cells is an excellent biomarker for use in AGUS diagnoses, and can be used by a clinician with great advantage as an adjunct in determining which AGUS diagnoses are likely yield significant lesions. This has a distinct cost-benefit potential since it has been shown that only approximately 40% of AGUS diagnoses are correspondingly associated with significant lesions (see Table 1).

Although the present invention has been described in considerable detail with reference to certain preferred versions thereof, other versions are possible. Therefore, the spirit and scope of the appended claims should not be limited to the description of the preferred versions described herein.

We claim:

1. A method for determining the presence of cancerous or pre-cancerous cervical lesions from Pap smear cells that have been cytologically diagnosed as atypical glandular cells of undetermined significance (AGUS) under the Bethesda System of terminology, said Pap smear including atypical and normal endocervical cells, said method comprising:

(A) subjecting said AGUS-diagnosed Pap smear cells to a procedure whereby MN/CA9 antigen is detected;

(B) observing the distribution of MN/CA9 antigen on atypical or normal cells of said AGUS cytologically diagnosed Pap smear cells;

(C) diagnosing the presence of significant lesions based on the observation of said MN/CA9 antigen on said atypical cells, wherein the significant lesions include adenocarcinoma, invasive carcinoma (CA), or high grade squamous intraepithelial lesions (HSIL); and (D) diagnosing the presence of low grade lesions based on the observation that said MN/CA9 antigen is absent from said atypical cells but is present on said normal endocervical cells, wherein the low grade lesions include low grade squamous intraepithelial lesions (LSIL) or atypia.

2. The method of claim 1, further comprising:

(E) diagnosing a benign condition based on the observation that said MN/CA9 antigen is absent from said atypical cells and normal endocervical cells.

3. A method for determining the presence of adenocarcinoma from Pap smear cells that have been cytologically diagnosed as atypical glandular cells of undetermined significance (AGUS) under the Bethesda System of terminology, said Pap smear including atypical and normal endocervical cells, said method comprising:

(A) subjecting said AGUS-diagnosed Pap smear cells to a procedure whereby MN/CA9 antigen is detected;

(B) observing the distribution of MN/CA9 antigen on atypical or normal cells of said AGUS cytologically diagnosed Pap smear cells; and (C) diagnosing the presence of adenocarcinoma based on the observation of said MN/CA9 antigen on said atypical cells in a honeycomb configuration.

4. The method of claim 3, wherein said adenocarcinoma is adenocarcinoma in situ (AIS) or invasive adenocarcinoma.

5. A method for determining the presence of high grade squamous intraepithelial lesions from Pap smear cells that have been cytologically diagnosed as atypical glandular cells of undetermined significance (AGUS) under the Bethesda System of terminology, said Pap smear including atypical and normal endocervical cells, said method comprising:

(A) subjecting said AGUS-diagnosed Pap smear cells to a procedure whereby MN/CA9 antigen is detected;

(B) observing the distribution of MN/CA9 antigen on atypical or normal cells of said AGUS cytologically diagnosed Pap smear cells; and:

(C) diagnosing the presence of high grade squamous intraepithelial lesions (HSIL) based on the observation of said MN/CA9.antigen on said atypical cells in a tight cluster.

6. A method for determining the presence of significant cancerous or pre-cancerous cervical lesions from Pap smear cells that have been cytologically diagnosed as atypical glandular cells of undetermined significance (AGUS) under the Bethesda System of terminology, said Pap smear including atypical and normal endocervical cells, said method comprising:

(A) subjecting said AGUS-diagnosed Pap smear cells to a procedure whereby MN/CA9 antigen is detected;

(B) observing the distribution of MN/CA9 antigen on atypical or normal cells of said AGUS cytologically diagnosed Pap smear cells;

(C) diagnosing the presence of significant lesions based on the observation of said MN/CA9 antigen on said atypical cells, wherein the significant lesions include adenocarcinoma, invasive carcinoma, or high grade intraepithelial lesions;

(D) diagnosing the presence of adenocarcinoma based on the observation of said MN/CA9 antigen on said atypical cells in a honeycomb configuration; and (E) diagnosing the presence of high grade squamous intraepithelial lesions (HSIL) based on the observation of said MN/CA9 antigen on said atypical cells in a tight cluster.

7. A method for determining the presence of low grade cervical lesions from Pap smear cells that have been cytologically diagnosed as atypical glandular cells of undetermined significance (AGUS) under the Bethesda System of terminology, said Pap smear including atypical and normal endocervical cells, said method comprising:

(A) subjecting said AGUS-diagnosed Pap smear cells to a procedure whereby MN/CA9 antigen is detected;

(B) observing the distribution of MN/CA9 antigen on atypical and normal cells of said AGUS cytologically diagnosed Pap smear cells; and (C) diagnosing the presence of low grade squamous intraepithelial lesions (LSIL) or atypia based on the observation that said MN/CA9 antigen is absent from said atypical cells but is present on said normal endocervical cells.

8. A method for determining the presence or absence of cancerous or pre-cancerous cervical lesions from Pap smear cells that have been cytologically diagnosed as atypical glandular cells of undetermined significance (AGUS) under the Bethesda System of terminology, said Pap smear including atypical and normal endocervical cells, said method comprising:

(A) subjecting said AGUS-diagnosed Pap smear cells to a procedure whereby a characterizing fraction of an MN/CA9 protein is detected, said characterizing fraction comprising at least one antigenic determinant or immunoreactive epitope of the MN/CA9 protein, which binds detectably to an anti-MN/CA9 antibody; and (B) observing the distribution of MN/CA9 antigen on atypical or normal cells of said AGUS cytologically diagnosed Pap smear;

(C) diagnosing the presence of adenocarcinoma, based on the observation of said MN/CA9 antigen on said atypical cells in a honeycomb configuration;

(D) diagnosing the presence of high grade squamous intraepithelial lesions (HSIL) based on the observation of said MN/CA9 antigen on said atypical cells in a tight cluster;

(E) diagnosing the presence of low grade squamous intraepithelial lesions (LSIL) and/or atypia based on the observation that said MN/CA9 antigen is absent from said atypical cells but is present on said normal endocervical cells; and (F) diagnosing a benign condition based on the observation that said MN/CA9 antigen is absent from said atypical cells and normal endocervical cells.

9. The method of claim 8, wherein said MN/CA9 antigen is detected by immunohistochemistry.

* * * * *

(12) EX PARTE REEXAMINATION CERTIFICATE (5308th)
United States Patent
Liao et al.

(10) Number: US 6,379,907 C1
(45) Certificate Issued: Mar. 21, 2006

(54) DIAGNOSTIC METHOD USING EXPRESSION OF MN/CA9 PROTEIN IN AGUS PAP SMEARS

(75) Inventors: Shu-Yuan Liao, Anaheim, CA (US); Eric J. Stanbridge, Corona del Mar, CA (US)

(73) Assignee: The Regents of the University of California, Oakland, CA (US)

Reexamination Request:
No. 90/006,318, Jul. 3, 2002
No. 90/006,667, Jun. 12, 2003

Reexamination Certificate for:
Patent No.: 6,379,907
Issued: Apr. 30, 2002
Appl. No.: 09/461,938
Filed: Dec. 15, 1999

Related U.S. Application Data

(60) Provisional application No. 60/147,556, filed on Aug. 5, 1999.

(51) Int. Cl.
*G01N 33/574* (2006.01)
*G01N 33/53* (2006.01)
*G01N 33/567* (2006.01)
*C12Q 1/00* (2006.01)
*C12Q 1/68* (2006.01)

(52) U.S. Cl. .............. 435/7.23; 435/4; 435/6; 435/7.1; 435/7.2; 436/64; 436/501; 436/503

(58) Field of Classification Search ............ 435/4, 435/6, 7.1, 7.2, 7.23; 436/64, 501, 503
See application file for complete search history.

(56) References Cited

U.S. PATENT DOCUMENTS 6,297,051 B1 * 10/2001 Zavada et al.

OTHER PUBLICATIONS

Liao, S.–Y., and E.J. Stanbridge, Cancer Epidemiology, Biomarkers & Prevention, 5(7): 549–557, 1996.*
DeMay, R.M., The art and science of cytopathology, vol. 1, Exfoliative cytology. American Society of Clinical Pathologists Press; Chicago, Il, 1996, p. 173 and pp. 120–121.*
Liao and Stanbridge, *Laboratory Investigation*, 76(1): 36A (Jan. 1997).
Liao and Stanbridge, *Cancer Epidemiology, Biomarkers & Prevention*, 5: 549–557 (Jul. 1996).
Liao et al., *Am. J. Pathol.*, 145(3): 598–609 (Sep. 1994).
Liao and Stanbridge, Abstract presented at the 83rd Annual Meeting in San Francisco of the U.S. and Canadian Academy of Pathology (Mar. 12–18, 1994) entitled "Analysis of MN Antigen Expression in Cervical Smears Indicates its Utility as a Diagnostic Marker of Cervical Neoplasia and Malignancy" (1994).
Bose et al., *A.J.C.P.*, 101(6): 708–713 (Jun. 1994).
Abstract of the 1997 Annual Meeting of the United States and Canadian Academy of Pathology bearing the heading Laboratory Investigation, 76(1):36A, entitled "Cervical Neoplasm Detected by MN Expression in Pap Smears of Atypical Glandular Cells of Undetermined Significant (AGUS)", Jan. 1997, Liao et al.

* cited by examiner

*Primary Examiner*—Alana M. Harris

(57) ABSTRACT

Determining the presence of cancerous or pre-cancerous cervical lesions from AGUS-diagnosed Pap smear cells by observing the distribution of MN/CA9 antigen expressed on atypical or normal cells and diagnosing (a) significant lesions when MN/CA9 antigen is observed on atypical cells, (b) low grade lesions when MN/CA9 antigen is absent from atypical cells but is present on normal endocervical cells, and (c) a benign condition when MN/CA9 antigen is absent from both atypical cells and normal endocervical cells.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 3, 4 and 5 is confirmed.

Claims 1, 2, 6, 7, 8 and 9 were previously disclaimed.

* * * * *